(12) United States Patent
Oskin et al.

(10) Patent No.: US 8,834,357 B2
(45) Date of Patent: Sep. 16, 2014

(54) STEERING MECHANISM

(75) Inventors: Christopher Oskin, Grafton, MA (US); Isaac Ostrovsky, Wellesley, MA (US); David W. Robertson, Framingham, MA (US); Michael Barenboym, Framingham, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 838 days.

(21) Appl. No.: 12/612,961

(22) Filed: Nov. 5, 2009

(65) Prior Publication Data

US 2010/0121147 A1 May 13, 2010

Related U.S. Application Data

(60) Provisional application No. 61/113,621, filed on Nov. 12, 2008.

(51) Int. Cl.
 *A61B 1/00* (2006.01)
 *A61B 1/005* (2006.01)
 *A61M 25/01* (2006.01)

(52) U.S. Cl.
 CPC .......... *A61M 25/0136* (2013.01); *A61B 1/0051* (2013.01)
 USPC ............................ 600/146; 600/149; 600/131

(58) Field of Classification Search
 USPC ......... 600/146, 147, 148, 149, 150, 151, 152; 604/95.04, 95.05
 See application file for complete search history.

(56) References Cited

U.S. PATENT DOCUMENTS

| | | | |
|---|---|---|---|
| 3,788,303 A * | 1/1974 | Hall | 600/148 |
| 4,566,437 A | 1/1986 | Yamaguchi | |
| 4,617,915 A | 10/1986 | Arakawa | |
| 4,998,916 A | 3/1991 | Hammerslag et al. | |

(Continued)

FOREIGN PATENT DOCUMENTS

| | | |
|---|---|---|
| DE | 26 00 493 A1 | 7/1977 |
| DE | 26 03 370 A1 | 8/1977 |

(Continued)

OTHER PUBLICATIONS

International Search Report and Written Opinion for International Application No. PCT/US09/63806, mailed on Jan. 20, 2010; 13 pages.

(Continued)

*Primary Examiner* — Anhtuan T Nguyen
*Assistant Examiner* — Jae Woo
(74) *Attorney, Agent, or Firm* — Bookoff McAndrews, PLLC

(57) ABSTRACT

A steering mechanism is used as part of a medical device such as a catheter or an endoscope to allow movement of a steerable distal portion of the catheter or endoscope. The mechanism can include a elongate housing adapted to be coupled to the steerable portion of the medical device and an actuation system including an actuator, a first cam, and a second cam. The actuator can move the first cam between a first position and a second position along a first axis (or about a second axis different than the first axis) to move the steerable portion of the medical device along a first plane. The actuator can move the second cam between a first position and a second position along the second axis (or about the first axis) to move the steerable portion of the medical device along a second plane different than the first plane.

17 Claims, 11 Drawing Sheets

(56) References Cited

U.S. PATENT DOCUMENTS

| | | | |
|---|---|---|---|
| 5,060,660 A | 10/1991 | Gambale et al. | |
| 5,105,819 A * | 4/1992 | Wollschlager et al. | 600/463 |
| 5,281,214 A | 1/1994 | Wilkins et al. | |
| 5,325,845 A | 7/1994 | Adair | |
| 5,347,989 A * | 9/1994 | Monroe et al. | 600/131 |
| D351,652 S | 10/1994 | Thompson et al. | |
| 5,352,237 A | 10/1994 | Rodak et al. | |
| 5,413,107 A | 5/1995 | Oakley et al. | |
| 5,611,777 A | 3/1997 | Bowden et al. | |
| 5,656,030 A | 8/1997 | Hunjan et al. | |
| 5,658,238 A * | 8/1997 | Suzuki et al. | 600/150 |
| 5,667,476 A | 9/1997 | Frassica et al. | |
| 5,702,349 A | 12/1997 | Morizumi | |
| 5,860,953 A | 1/1999 | Snoke et al. | |
| 5,882,333 A | 3/1999 | Schaer et al. | |
| 5,897,529 A | 4/1999 | Ponzi | |
| 5,906,590 A | 5/1999 | Hunjan et al. | |
| 5,957,865 A | 9/1999 | Backman et al. | |
| 6,007,531 A | 12/1999 | Snoke et al. | |
| 6,027,473 A | 2/2000 | Ponzi | |
| 6,059,739 A | 5/2000 | Baumann | |
| 6,066,125 A | 5/2000 | Webster, Jr. | |
| 6,123,699 A | 9/2000 | Webster, Jr. | |
| 6,171,277 B1 | 1/2001 | Ponzi | |
| 6,183,435 B1 | 2/2001 | Bumbalough et al. | |
| 6,183,463 B1 | 2/2001 | Webster, Jr. | |
| 6,198,974 B1 | 3/2001 | Webster, Jr. | |
| 6,203,507 B1 | 3/2001 | Wadsworth et al. | |
| 6,267,746 B1 | 7/2001 | Bumbalough | |
| 6,468,260 B1 | 10/2002 | Bumbalough et al. | |
| 6,500,167 B1 | 12/2002 | Webster, Jr. | |
| 6,571,131 B1 | 5/2003 | Nguyen | |
| 6,605,086 B2 | 8/2003 | Hayzelden et al. | |
| 6,679,873 B2 | 1/2004 | Rabiner et al. | |
| 6,783,510 B1 | 8/2004 | Gibson et al. | |
| 6,793,622 B2 * | 9/2004 | Konomura et al. | 600/152 |
| 6,802,835 B2 | 10/2004 | Rabiner et al. | |
| 6,837,867 B2 | 1/2005 | Kortelling | |
| 6,945,956 B2 | 9/2005 | Waldhauser et al. | |
| 6,966,906 B2 | 11/2005 | Brown | |
| 7,037,290 B2 | 5/2006 | Gardeski et al. | |
| 7,060,024 B2 | 6/2006 | Long et al. | |
| 7,060,025 B2 | 6/2006 | Long et al. | |
| 7,115,134 B2 | 10/2006 | Chambers | |
| 7,232,437 B2 | 6/2007 | Berman et al. | |
| 7,238,180 B2 | 7/2007 | Mester et al. | |
| 8,048,025 B2 * | 11/2011 | Barenboym et al. | 604/95.04 |
| 8,057,462 B2 * | 11/2011 | Weitzner et al. | 606/1 |
| 2004/0059191 A1 * | 3/2004 | Krupa et al. | 600/146 |
| 2004/0193016 A1 * | 9/2004 | Root et al. | 600/146 |
| 2004/0193239 A1 | 9/2004 | Falwell et al. | |
| 2005/0080476 A1 | 4/2005 | Gunderson et al. | |
| 2005/0256375 A1 | 11/2005 | Freed | |
| 2005/0277874 A1 | 12/2005 | Selkee | |
| 2005/0277875 A1 | 12/2005 | Selkee | |
| 2005/0288627 A1 | 12/2005 | Mogul | |
| 2006/0142694 A1 | 6/2006 | Bednarek et al. | |
| 2006/0173448 A1 | 8/2006 | Scheller et al. | |
| 2006/0252993 A1 | 11/2006 | Freed et al. | |
| 2007/0156116 A1 | 7/2007 | Gonzalez | |
| 2007/0203474 A1 | 8/2007 | Ryan et al. | |
| 2007/0219529 A1 | 9/2007 | Abe et al. | |
| 2007/0270647 A1 | 11/2007 | Nahen et al. | |
| 2007/0282167 A1 * | 12/2007 | Barenboym et al. | 600/131 |
| 2007/0299387 A1 * | 12/2007 | Williams et al. | 604/22 |
| 2008/0051802 A1 | 2/2008 | Schostek et al. | |
| 2009/0171275 A1 | 7/2009 | Ostrovsky et al. | |
| 2010/0049000 A2 * | 2/2010 | Tanaka | 600/149 |

FOREIGN PATENT DOCUMENTS

| | | |
|---|---|---|
| EP | 0 521 595 B1 | 5/1999 |
| EP | 0 668 052 B1 | 1/2003 |
| WO | WO 93/20878 A | 10/1993 |
| WO | WO 2007/136829 A1 | 11/2007 |

OTHER PUBLICATIONS

International Search Report and Written Opinion for PCT/US07/11912, mailed on Sep. 12, 2008; 8 pages.
International Preliminary Report on Patentability for PCT/US07/11912, mailed in Dec. 4, 2008; 6 pages.
International Search Report and Written Opinion for PCT/US08/86142, mailed on Mar. 11, 2009; 10 pages.
International Search Report and Written Opinion for PCT/US09/34831, mailed on May 13, 2009; 13 pages.
International Search Report and Written Opinion for PCT/US09/48792, mailed on Sep. 22, 2009; 15 pages.
International Search Report and Written Opinion for PCT/US09/49809, mailed on Oct. 28, 2009; 10 pages.

* cited by examiner

STEERING MECHANISM

CROSS-REFERENCE TO RELATED APPLICATIONS

This application claims priority to and the benefit of Provisional U.S. Patent Application Ser. No. 61/113,621, filed Nov. 12, 2008, the entirety of which is incorporated herein by reference.

TECHNICAL FIELD

The invention generally relates to a mechanism for controlling articulation of a steerable portion of a medical device, and more particularly to a steering mechanism that utilizes a mechanical advantage to control articulation of the steerable portion on at least two planes.

BACKGROUND INFORMATION

Steering mechanisms are used to steer or direct a medical instrument, for example a catheter or endoscope, to a desired position or location in a body of a patient. One known steering mechanism resembles a joystick. The configuration of the joystick usually includes a plate attached to control wires. The plate, however, must be large to accommodate the desired articulations of the steerable medical device. Additionally, the single control element encompassed in the joystick control mechanism makes the introduction of force leverage difficult, especially in a procedure during which an increased leverage is needed for different articulation planes.

Another known steering mechanism includes multiple slidable buttons. Each button is connected to a puller wire so that when the button is moved, the puller wire moves the catheter in a single direction associated with the puller wire. Thus, at least four slidable buttons are required to achieve 360 degree articulation of the catheter or endoscope. The sliding motion of the buttons on this steering mechanism makes introduction of force leverage very difficult.

SUMMARY OF THE INVENTION

It is an object of the invention to allow steering operation of a steerable portion of a medical device along multiple planes. A steering mechanism according to the invention can control articulation of a steerable portion of a medical device along at least two different planes. A steering mechanism according to the invention can also introduce a mechanical advantage, e.g. force leverage, during operation of the steering mechanism to move the steerable portion of the medical device along each plane.

In one aspect, the invention relates to a steering mechanism for use as part of a medical device. The steering mechanism can comprise an elongate housing and an actuation system. The housing is adapted to be coupled to a steerable member of a medical device. The actuation system is coupled to the elongate housing. The actuation system is adapted to control movement of the steerable member of the medical device within a body of a patient. The actuation system includes an actuator, a first cam, and a second cam. The actuator is adapted to move the first cam from a first position to a second position different than the first position when the actuator is moved in a first direction about a first axis. The first cam is adapted to move the steerable member of the medical device in a first direction along a first plane when the first cam is moved from the first position to the second position. The actuator is adapted to move the second cam from a first position to a second position different than the first position when the actuator is moved in a first direction about a second axis different than the first axis. The second cam is adapted to move the steerable member of the medical device in a first direction along a second plane when the second cam is moved from the first position to the second position.

Embodiments according to this aspect of the invention can include various features. For example, the steering mechanism can include a protrusion coupled to the first cam. The protrusion is adapted to move in a first direction when the actuator is moved in its first direction along the second axis and is adapted to engage a portion of the second cam as the protrusion is moved in its first direction. The protrusion can be adapted to move the second cam from its first position to its second position as the protrusion is moved in the first direction.

In another example, the elongate housing of the steering mechanism can include a first grip portion and a second grip portion different than the first grip portion. The actuator can be coupled to the elongate housing between the first grip portion and the second grip portion. The elongate housing is adapted to be in a first orientation when operatively held by the first grip portion. The first orientation of the elongate housing can be a substantially horizontal orientation. The elongate housing is adapted to be in a second orientation different than the first orientation when operatively held by the second grip portion. The second orientation of the elongate housing can be a substantially vertical orientation.

In some embodiments, at least a portion of the elongate housing including a distal end portion of the elongate housing substantially extends along the first axis. In some embodiments, at least a portion of the elongate housing including a proximal end portion of the elongate housing substantially extends along an axis different than the first axis.

In another example, the first cam and the second cam are adapted to rotate about the second axis. In some embodiments, the actuator is adapted to move the first cam from its second position to at least one of the first position or a third position different than the first position when the actuator is moved in a second direction different than the first direction about the first axis. The first cam can be adapted to move the steerable member in a second direction different than the first direction along the first plane when the first cam is moved from the second position to the at least one of the first position or the third position. The actuator can be adapted to move the second cam from the second position to at least one of the first position and a third position different than the third position when the actuator is moved in a second direction different than the first direction about the second axis. The second cam can be adapted to move the steerable member in a second direction different than the first direction along the second plane when the second cam is moved from the second position to the at least one of the first position or the third position.

In some embodiments, the first cam is adapted to be moved from its first position to its second position independently of movement of the second cam from its first position to its second position. In some embodiments, the second cam is adapted to be moved from its first position to its second position independently of movement of the second cam from its first position to its second position.

In yet another example, the steering mechanism can further comprise a Bowden cable disposed over a portion of a wire coupled to the actuator. The Bowden cable is adapted to move relative to the wire when the wire is moved in response to movement of the actuator.

In some embodiments, the actuation system is adapted for one-fingered operation by a user. In some embodiments, the actuator is movable in the first direction along the first axis and in the first direction along the second axis substantially simultaneously.

In another aspect, the invention generally involves a steering mechanism for use with or as part of a medical device and that includes a housing, an actuator, a first cam, and a second cam. The housing is adapted to be coupled to a medical device including a steerable portion. At least a portion of the housing extends along a first axis. The actuator is coupled to the housing and is movable with respect to the housing in a first direction about the first axis. The actuator is movable with respect to the housing in a first direction about a second axis different than the first axis. The first cam is movable in response to movement of the actuator in the first direction about the second axis. The first cam is adapted to move the steerable portion of the medical device along a first plane. The second cam is movable in response to movement of the actuator in the first direction about the first axis. The second cam is adapted to move the steerable portion of the medical device along a second plane different than the first plane.

Embodiments according to this other aspect of the invention can include various features. For example, the actuator can be adapted for one-fingered operation by a user. The actuator can be adapted to control movement of the steerable portion of the medical device along the first plane and the second plane such that 360 degree articulation of a portion of the steerable portion is achievable.

In another example, the first cam can be adapted to move about the first axis and the second axis different than the first axis.

In another example, the steering mechanism further comprises a protrusion that is adapted to engage a portion of the second cam as the actuator moves in the first direction about the first axis. The protrusion can be adapted to move the second cam from a first position to a second position different than the first position. The second cam can be adapted to move the steerable portion of the medical device in a first direction along the second plane as the second cam moves from its first position to its second position.

In yet another example, the steering mechanism further comprises a wire and a Bowden cable. The wire is coupled to the actuator and is adapted to move the steerable member of the medical device. The Bowden cable is disposed over at least a portion of the wire. The wire is movable with respect to the Bowden cable.

In still another example, the elongate housing is adapted to be selectively held in a substantially horizontal orientation and a substantially vertical orientation during operation of the steering mechanism to control movement of the steerable member in a body of a patient.

DESCRIPTION

Apparatuses for controlled articulation of a steerable device are described herein. For example, in some embodiments, the apparatus is a steering mechanism for use as part of a medical device. The steering mechanism can be used as part of or with a medical device including a steerable member or portion, such as, for example, a catheter or endoscope.

Figure 1:
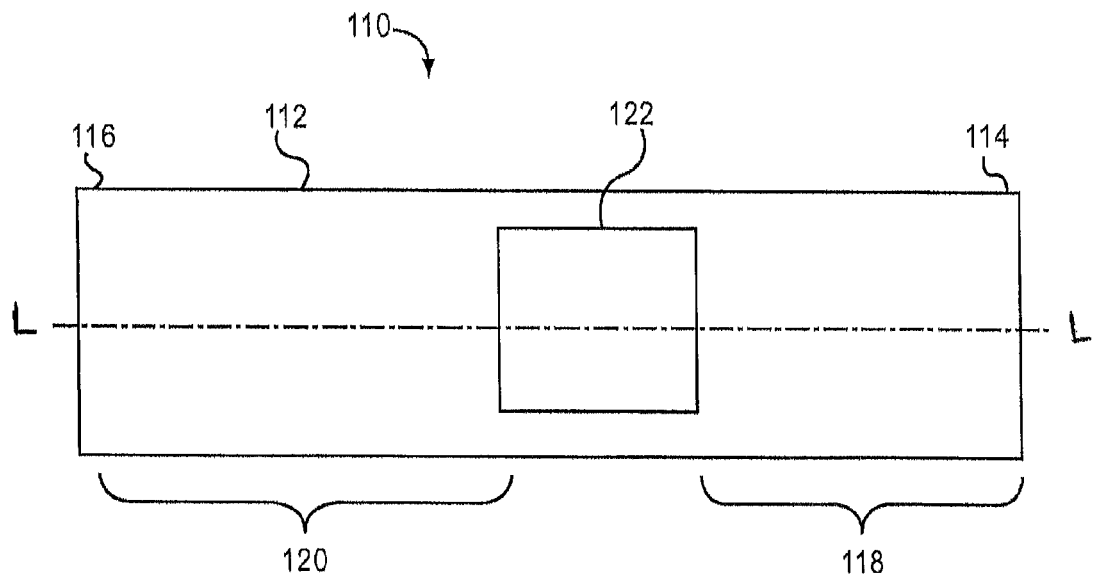
FIG. 1 is a schematic illustration of a steering mechanism for use with or as part of a medical device according to an embodiment of the invention.

In one embodiment, as schematically illustrated in FIG. 1, the apparatus 110 is a steering mechanism. The steering mechanism 110 includes an elongate housing 112 and an actuator 122. The elongate housing 112 (also referred to herein as "housing") is configured to be coupled to a device including a steerable member (not illustrated in FIG. 1).

The elongate housing 112 includes a first grip portion 118 and a second grip portion 120 different than the first grip portion. The elongate housing 112 is adapted to be held by a single hand of a user. The elongate housing 112 is adapted to be held in at least two orientations during use, as described in more detail herein. For example, the elongate housing 112 is adapted to be in a first orientation when operatively held by the first grip portion 118 of the elongate housing. The elongate housing 112 is adapted to be in a second orientation different than the first orientation when operatively held by the second grip portion 120 of the elongate housing. The phrase "operatively held" as used herein means when a user holds the device in a manner consistent with the intended use and operation of the device; for example, as the user would hold the device while using the device to treat a patient.

The elongate housing 112 includes a proximal end portion 114 and a distal end portion 116. At least a portion of the elongate housing 112 substantially extends along an axis L.

The actuator 122 is coupled to the elongate housing 112. In the embodiment illustrated in FIG. 1, the actuator 122 is coupled to a portion of the elongate housing 112 between the first grip portion 118 and the second grip portion 120 of the elongate housing.

The actuator 122 is adapted for one-fingered operation by a user. The actuator 122 is adapted to control movement of a portion of a steerable member of a medical device along at least a first plane and a second plane different than the first plane such that the portion of the steerable member of the medical device is movable in substantially any direction 360 degrees around a central axis (not illustrated in FIG. 1).

Figure 2:
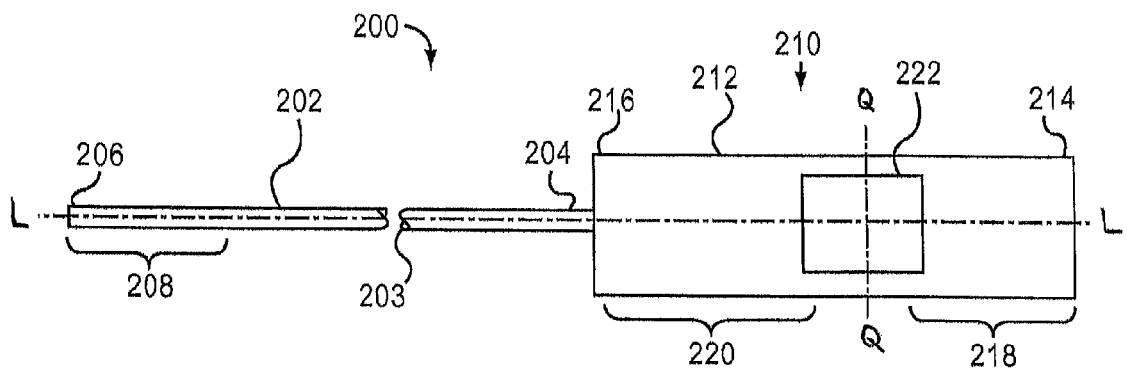
FIG. 2 is a schematic illustration of a medical device according to an embodiment of the invention.

In FIG. 2, the apparatus 200 is a steerable medical device (also referred to herein as "medical device" or "steerable device"). The steerable medical device 200 includes an elongate member 202 (also referred to herein as "steerable member") and a steering mechanism 210.

The steering mechanism 210 is substantially similar to the steering mechanism 110 described above and with reference to FIG. 1. The steering mechanism 210 is adapted to control movement (or articulation) of at least a portion of the elongate member 202. The steering mechanism 210 is adapted to move the portion of the elongate member 202 along the first plane and the second plane.

The elongate member 202 includes a proximal end portion 204 and a distal end portion 206 and defines a lumen 203 therethrough. At least a portion of the elongate member 202 is configured to be steerable. Said another way, in some embodiments, the elongate member 202 includes a steerable portion 208. As described in more detail below, the steerable portion 208 of the elongate member 202 is movable along the first plane and the second plane. For example, in some embodiments, the steerable portion 208 is movable along a vertical plane and a horizontal plane.

In some embodiments, the elongate member 202 is a catheter or endoscope. For example, the elongate member can be a ureteroscope, boroscope, or colonoscope. Because the elongate member 202 is movable along the first plane and the second plane different than the first plane, a user can steer the elongate member through tortuous paths within a body of a patient. For example, the user can selectively operate the steerable device 200 to navigate a catheter through a tortuous bodily vessel.

The steering mechanism 210 is coupled to the elongate (or steerable) member 202. The steering mechanism 210 includes an elongate housing 212 and an actuator 222. The elongate housing 212 includes a proximal end portion 214 and a distal end portion 216. In the embodiment illustrated in FIG. 2, the distal end portion 216 of the elongate housing 212 is coupled to the proximal end portion 204 of the elongate member 202.

In some embodiments, the steering mechanism 210 is adapted for at least one of one-handed or one-fingered operation by a user. Said another way, a user can manipulate or control articulation of the steerable portion 208 of the elongate member 202 by operating the steering mechanism 210 with a single hand or finger.

For example, the user can selectively hold the steering mechanism 210 by a first grip portion 218 or a second grip portion 220. While holding either the first grip portion 218 and the second grip portion 220 with his hand, the user can place a finger of the same hand holding the elongate housing 212 on the actuator 222. The actuator 222 is movable (or operable) by the single finger of the user. As used herein, the word "finger" means any digit of a person's hand, including the thumb.

The actuator 222 is movable with respect to the elongate housing 212 in at least a first direction along axis L. As described in more detail herein, movement of the actuator 222 in the first direction along axis L moves at least a portion of the elongate member 202 in a first direction along the first plane (e.g., the steerable portion 208 of the elongate member 202).

The actuator 222 is movable with respect to the elongate housing 212 in at least a first direction along a different axis, axis Q, than axis L (or about axis L). For example, axis Q can be transverse or substantially normal to axis L, as illustrated in FIG. 2. Movement of the actuator 222 in the first direction along axis Q moves at least a portion of the elongate member 202 in a first direction along the second plane.

Figure 3:
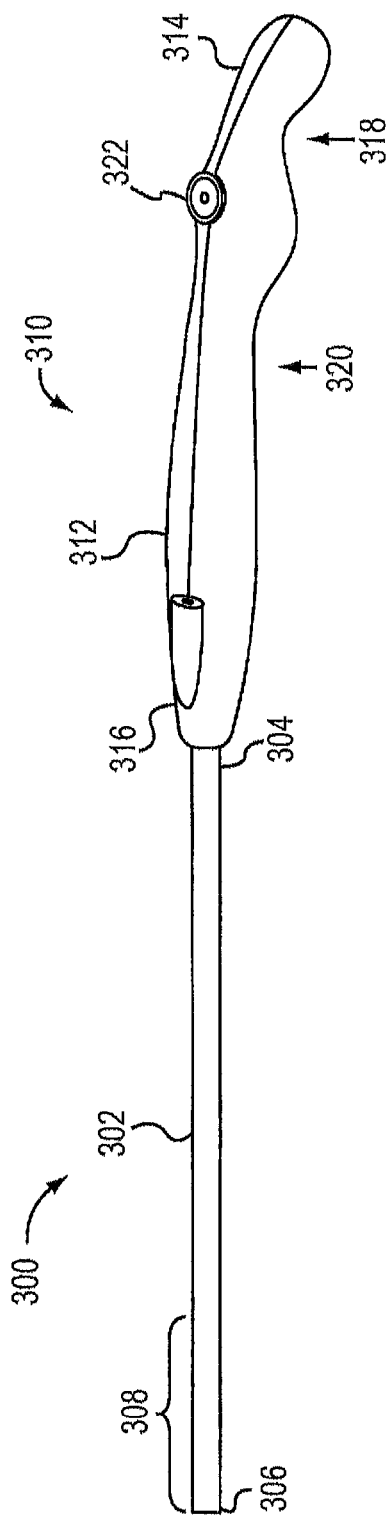
FIG. 3 is a perspective view of a medical device according to an embodiment of the invention.
Figure 4:
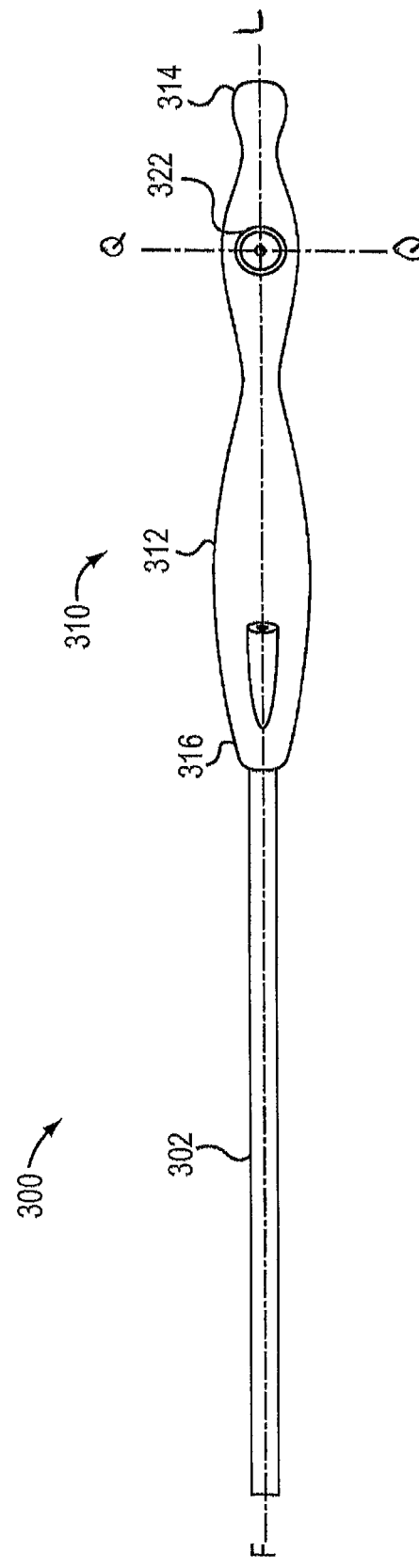
FIG. 4 is a top view of the medical device of FIG. 3.

As illustrated in FIGS. 3 and 4, an apparatus 300, or steerable medical device, according to an embodiment of the invention includes an elongate member 302 (also referred to herein as "steerable member") and a steering mechanism 310. The steering mechanism 310 substantially extends along axis L. The elongate member 302 substantially extends along a central axis. In the embodiment illustrated in FIG. 4, the central axis is axis L. In other embodiments, the central axis and axis L can be coaxial or non-coaxial.

As illustrated in FIG. 4, the elongate member 302 substantially extends along the central axis when the elongate member is in a non-articulated (or linear) position (also referred to as the "first position"). In some embodiments, the elongate member 302 is biased towards a linear or relaxed position.

Note that the illustrations in the figures are representative only, and are not drawn to scale. For example, in some embodiments, the elongate member is a catheter or endoscope of greater length (such as compared to the length of the steering mechanism) than the elongate member in the illustrated embodiment.

The elongate member 302 includes a proximal end portion 304 and a distal end portion 306 and defines a lumen 303 (illustrated in FIG. 5) at least partially therethrough. At least a portion of the elongate member 302 is a steerable portion 308. At least a portion of the steerable portion 308 is movable along at least a first plane and a second plane different than the first plane, such that the portion of the steerable portion 308 of the elongate member 302 is movable in substantially any direction 360 degrees around the central axis C.

The steering mechanism 310 is adapted to control movement (or articulation) of at least a portion of the elongate member 302 of the device 300. For example, in some embodiments, the steering mechanism 310 is configured to move the steerable portion 308 of the elongate member 302 along the first plane and along the second plane different than the first plane.

The steering mechanism 310 is adapted to be coupled to the elongate member 302. In some embodiments, the steering mechanism 310 is removably coupled to the elongate member 302.

The steering mechanism 310 includes an elongate housing 312 and an actuator 322. The elongate housing 312 includes a proximal end portion 314 and a distal end portion 316. The elongate housing 312 of the steering mechanism 310 is couplable to the elongate member 302. As illustrated in FIGS. 3 and 4, the distal end portion 316 of the elongate housing 312 is coupled to the elongate member 302.

Figure 5:
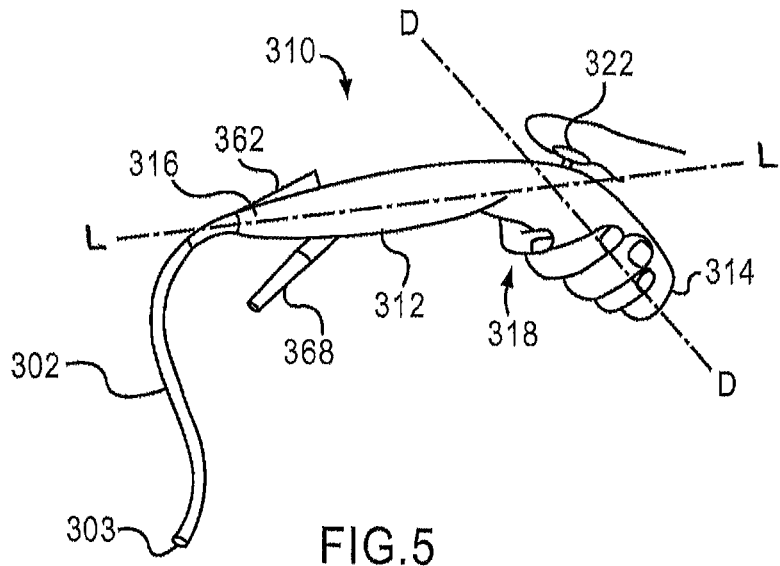
FIG. 5 is a side view of the medical device of FIG. 3 being held in a horizontal orientation by a hand of a user.

The elongate housing 312 includes a first grip portion 318 and a second grip portion 320 different than the first grip portion. Each of the first grip portion 318 and second grip portion 320 is adapted to be held or grasped by a hand of a user. The elongate housing 312 is adapted to be in a first orientation when the first grip portion 318 is operatively held by the hand of the user. For example, as illustrated in FIG. 5, when the user holds the elongate housing 312 of the steering mechanism 310 by the first grip portion 318, the elongate housing (and the steering mechanism) is in a substantially horizontal orientation. The user can operate the actuator 322 with a single finger of the hand holding the first grip portion 318.

Figure 6:
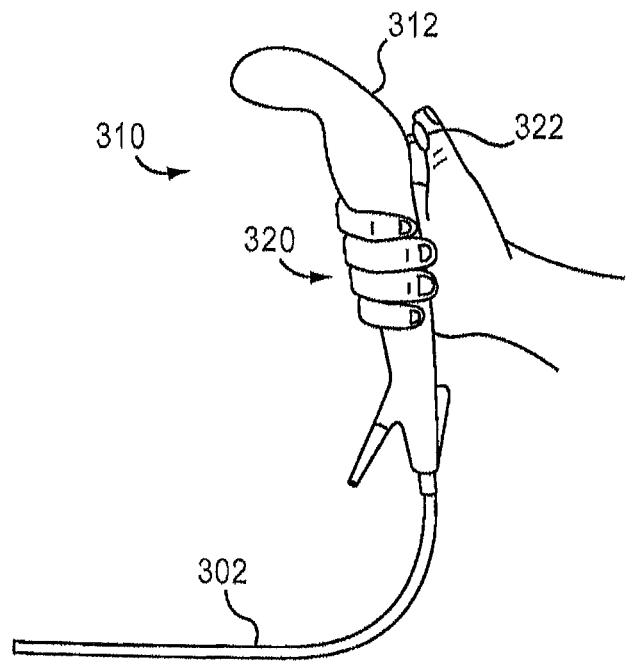
FIG. 6 is a side view of the medical device of FIG. 3 being held in a vertical orientation by a hand of a user.

The elongate housing 312 is adapted to be in a second orientation different than the first orientation when the second grip portion 320 is held by the hand of the user. For example, as illustrated in FIG. 6, when the user holds the elongate housing 312 of the steering mechanism 310 by the second grip portion 320, the elongate housing (and the steering mechanism) is in a substantially vertical orientation. The user can operate the actuator 322 with a single finger of the hand holding the second grip portion 320.

At least one of the first grip portion 318 and the second grip portion 320 can be contoured. For example, a contoured first or second grip portion 318, 320 can provide a more ergonomic handle for the steering mechanism 310. As illustrated in FIGS. 3-6, the first grip portion 318 and the second grip portion 320 are each contoured. The first and second grip portions 318, 320 each define a waist in the elongate housing 312.

In some embodiments, the first and second grip portions 318, 320 are similar in size and/or shape. In other embodiments, the first and second grip portions 318, 320 are different in size and shape. For example, in some embodiments, only one of the first or second grip portions is contoured. In still other embodiments, no portion of the elongated member defines a contour, waist, or curve.

At least a portion of the elongate housing 312 substantially extends along axis L. As illustrated in FIGS. 4 and 5, a portion of the elongate housing 312 including the distal end portion 316 of the elongate housing extends along axis L.

In some embodiments, the elongate housing 312 is constructed such that the proximal end portion 314 of the elongate housing is offset from axis L. For example, as illustrated in FIG. 5, at least a portion of the elongate housing 312 including the proximal end portion 314 of the elongate housing substantially extends along an axis D different than axis L. In some embodiments, the elongate housing 312 is curved or includes a curved portion such that a portion of the elongate housing is offset from the axis L and/or extends along axis $A_D$. As illustrated in FIG. 5, the elongate housing 312 can be substantially similar in shape to a pistol or handgun.

Figure 7:
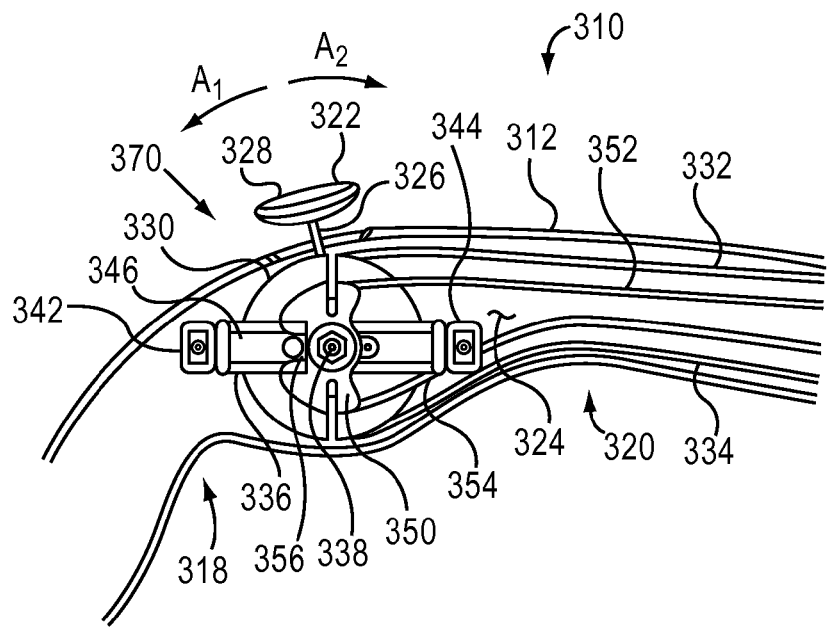
FIGS. 7 and 8 are side and perspective views, respectively, of a portion of a steering mechanism of the medical device of FIG. 3 with a portion of the elongate housing removed.
Figure 8:
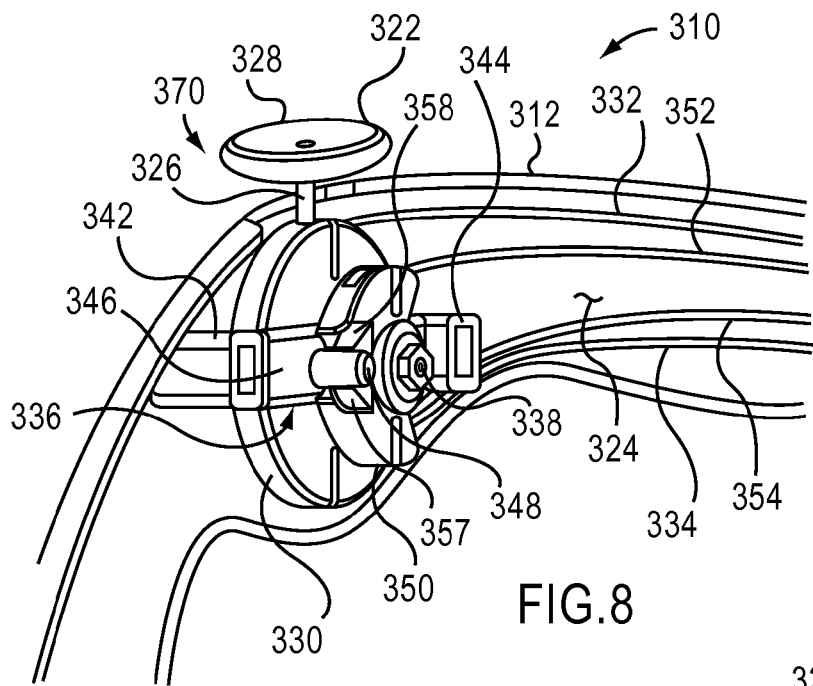

As illustrated in FIGS. 7 and 8, the elongate housing 312 defines a cavity 324. In some embodiments, the cavity 324 extends from the proximal end portion 314 to the distal end portion 316 of the elongate housing 312. In some embodiments, at least a portion of the actuator 322 is disposed in the cavity 324 of the elongate housing 312. For example, as illustrated in FIGS. 7 and 8, the actuator 322 includes a stem 326 that extends from a finger rest portion 328 of the actuator 322 exterior to the elongate housing 312 into the cavity 324 of the elongate housing. The elongate housing 312 defines an opening through which the stem 326 of the actuator 322 extends. Although the finger rest portion 328 is illustrated in the shape of a button in FIGS. 7 and 8, in other embodiments, the finger rest portion can be any known shape. The actuator 322 is adapted for one-fingered use by the user.

The actuator 322 is coupled to the elongate housing 312. In the illustrated embodiment, the actuator 322 is coupled to a portion of the elongate housing 312 between the first grip portion 318 and the second grip portion 320 of the elongate housing.

The actuator 322 is adapted to control movement of a portion of the steerable member 302 of the medical device 300 along at least the first plane and the second plane. As such, the actuator 322 can control movement of the steerable portion 308 of the steerable member 302 in substantially any direction 360 degrees around the central axis C.

The actuator 322 is movable in at least a first direction along axis L. As described in more detail below, movement of the actuator 322 in the first direction along axis L moves the steerable portion 308 of the medical device 300 in a first direction along the first plane. For example, in some embodiments, the first plane is a vertical plane, and thus movement of the actuator 322 in the first direction along axis L moves the steerable portion 308 in the first direction along the vertical plane (e.g., "up").

The actuator 322 is movable in a second direction different than the first direction along the axis L. For example, the actuator 322 can be moved in a second direction that is opposite the first direction along axis L. Movement of the actuator 322 in the second direction along axis L moves the steerable portion 308 of the medical device 300 in a second direction different than the first direction along the first plane. For example, movement of the actuator 322 in the second direction along axis L moves the steerable portion 308 in the second direction along the vertical plane (e.g., "down").

The actuator is movable in at least a first direction along axis Q (or about or around the axis L). As described in more detail below, movement of the actuator 322 in the first direction along axis Q moves the steerable portion of the medical device in at least a first direction along the second plane. For example, in some embodiments, the second plane is a horizontal plane, and thus movement of the actuator 322 in the first direction along axis Q moves the steerable portion 308 in the first direction along the horizontal plane (e.g., to the right).

The actuator 322 is movable in a second direction different than the first direction along axis Q. For example, the actuator 322 can be moved in a second direction that is opposite the first direction along axis Q. Movement of the actuator 322 in the second direction along axis Q moves the steerable portion 308 of the medical device 300 in a second direction along the second plane different than the first direction. For example, movement of the actuator 322 in the second direction along axis Q moves the steerable portion 308 in the second direction along the horizontal plane (e.g., to the left).

In some embodiments, as illustrated in FIGS. 7 and 8, the actuator 322 is included in an actuation system 370 of the steering mechanism 310. The actuation system 370 is adapted to control articulation of the steerable member 302. The actuation system 370 of the steering mechanism 310 includes the actuator 322, a first cam 330, a second cam 350, and first, second, third, and fourth wires 332, 334, 352, 354, or any combination of the foregoing.

The first cam 330 moves in response to movement of the actuator 322. The first cam 330 is adapted to move the steerable portion 308 of the medical device 300 along the first plane when the first cam moves in response to movement of the actuator 322.

As illustrated in FIG. 7, the first cam 330 is at least partially disposed in the cavity 324 of the elongate housing. The first cam 330 is coupled to the elongate housing 312 by a frame 336. The frame 336 is coupled to an inner surface of the elongate housing 312 defining the cavity 324. In the embodiment illustrated in FIGS. 7 and 8, the frame 336 includes a first supporting arm 342, a second supporting arm 344, and a central arm 346. The first supporting arm 342 and second supporting arm 344 are each coupled to the elongate housing 312. The central arm 346 extends between and is coupled to the first and second supporting arms 342, 344.

Figure 8A:
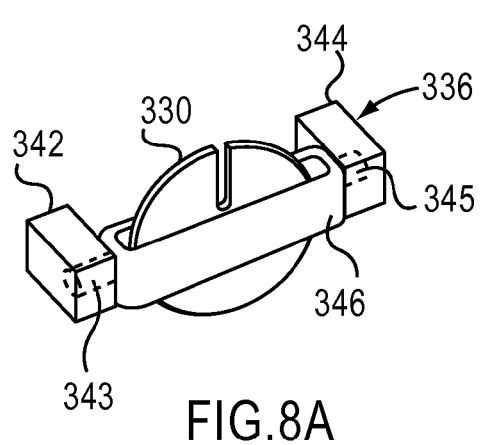
FIG. 8A is a perspective view of a portion of the steering mechanism of the medical device of FIG. 3.
Figure 9:
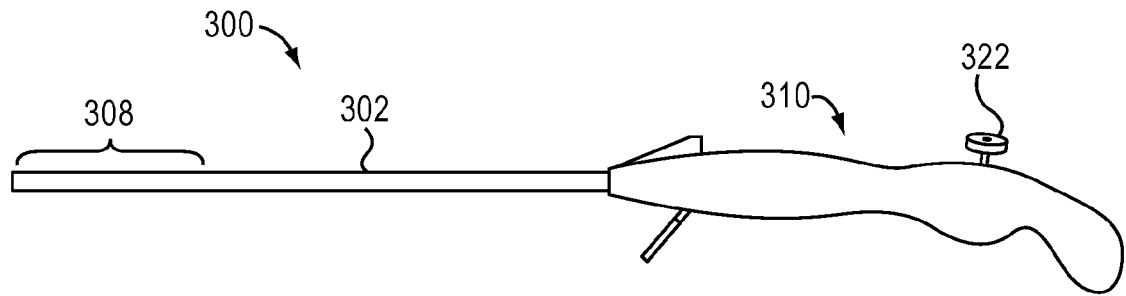
FIGS. 9-11 are side views of the medical device of FIG. 3 in a first, second, and third configuration, respectively.
Figure 10:
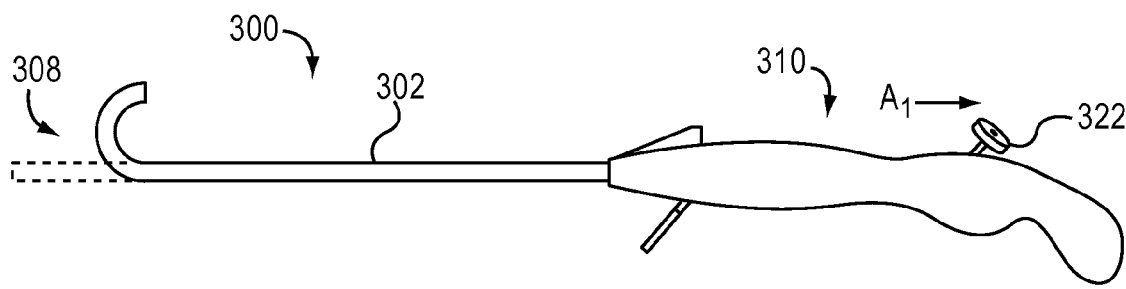
Figure 11:
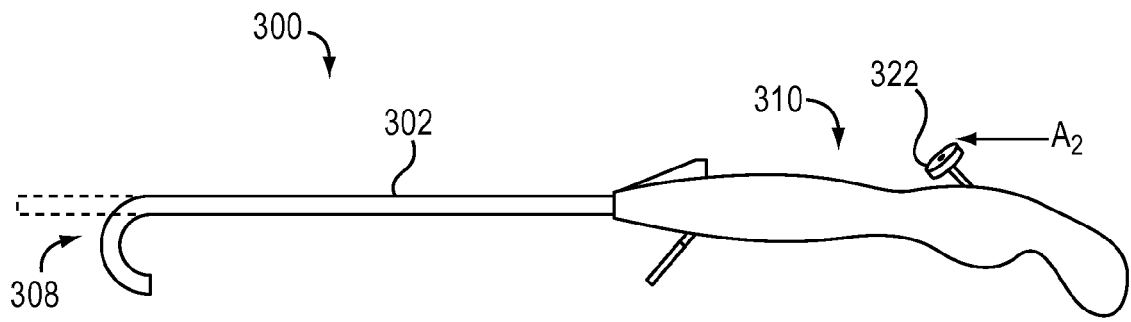
Figure 12:
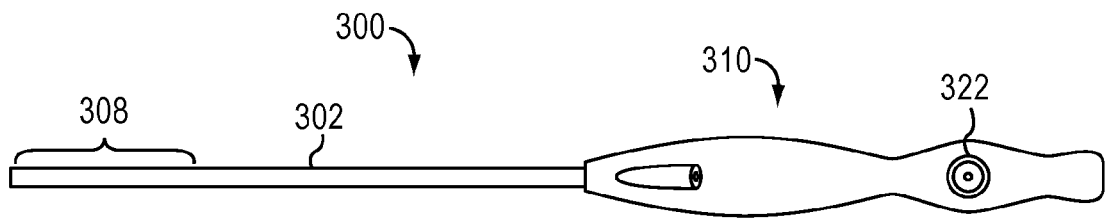
FIGS. 12-14 are side views of the medical device of FIG. 3 in a first, second, and third configuration, respectively.
Figure 13:
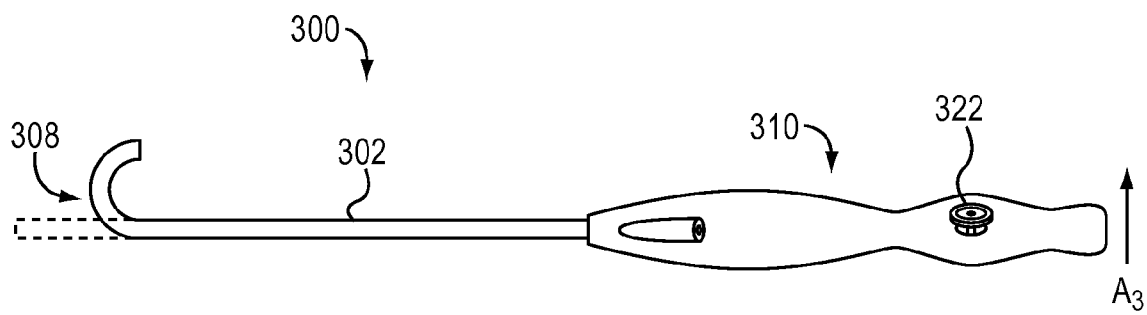
Figure 14:
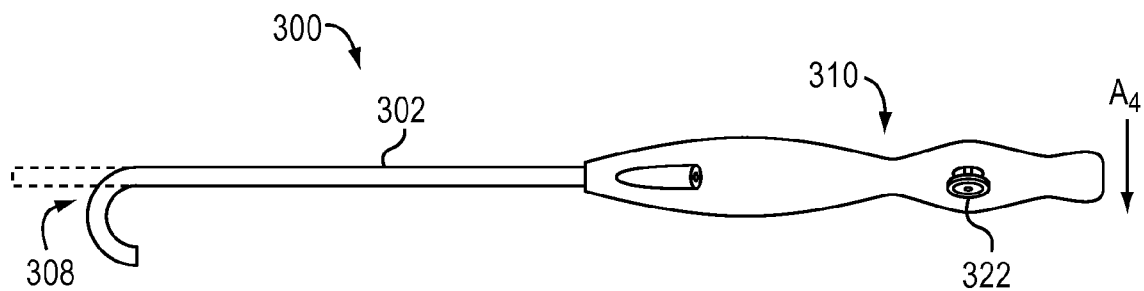

In the embodiment illustrated in FIG. 8A, the central arm 346 defines an opening or pocket adapted to receive a portion of the first cam 330. The first cam 330 is coupled to the central arm 346. The first cam 330 can be coupled to the central arm 346 by any known coupling mechanism, including, but not limited to, a pin or other mechanical fastener.

The first cam 330 is movable with respect to the frame 336. The first cam 330 is movable between at least a first position (illustrated in FIG. 7) and a second position different than the first position. In the embodiment illustrated in FIGS. 7-11, the first cam 330 is movable between at least the first position, the second position, and a third position different than the first and second positions, as described herein.

The first cam 330 is coupled to the actuator 322. In some embodiments, as illustrated in FIGS. 7 and 8, the first cam 330 is fixedly coupled to the stem 326 of the actuator 322.

The first cam 330 is coupled to each of the first wire 332 and the second wire 334. As illustrated in FIGS. 7 and 8, the first and second wires 332, 334 are coupled to the first cam 330 at spaced locations. The first wire 332 can be coupled to the first cam 330 proximate to the actuator 322. In the embodiment illustrated in FIG. 7, the second wire 334 is coupled to a portion of the first cam 330 different than the portion of the cam coupled to the first wire 332. The first wire 332 and the second wire 335 are each adapted to move in response to movement of the first cam 330. Additionally, the first and second wires 332, 334 are each coupled to the elongate member 302 of the medical device 300. Thus, movement of the first and second wires 332, 334 moves the elongate member 302, as described in more detail herein.

Referring to FIGS. 7 and 9-11, as the actuator 322 is moved in its first direction along axis L (as indicated by arrow $A_1$), the first cam 330 correspondingly moves to a second position different than its first position. As the first cam 330 moves towards its second position, the first cam moves (or pulls on) the first wire 332. The first wire 332 moves the steerable portion 308 of the elongate member 302 in its first direction along the first plane (e.g., "up").

To return the elongate member 302 to its starting position (or the linear or relaxed position), the actuator 322 is moved in its second direction until the first cam 330 is moved (or returned) to its first position. In some embodiments, at least one of the actuator 322 and the first cam 330 is biased towards a first (or starting) position.

As the actuator 322 is moved in its second direction along axis L (as indicated by arrow $A_2$), the first cam 330 correspondingly moves to a third position different than its first and second positions. As the first cam 330 moves from its first position towards its third position, the cam moves (or pulls on) the second wire 334. The second wire 332 moves the steerable portion of the elongate member 302 in its second direction along the first plane (e.g., "down").

The first cam 330 is adapted to introduce force leverage (or a mechanical advantage) to help move the elongate member 302 along the first plane when the steering mechanism 310 is operated. Because the first cam 330 moves by rotating about axis Q, the first cam is adapted to introduce force leverage; for example, to the first wire 332 and/or the second wire 334 as the first cam moves between its first, second, and/or third positions.

The second cam 350 is adapted to move the steerable portion 308 of the medical device 300 along the second plane when the second cam moves in response to movement of the actuator 322. As illustrated in FIGS. 7 and 8, the second cam 350 is at least partially disposed in the cavity 324 of the elongate housing 412.

The second cam 350 is coupled to the elongate housing 312 by a central axle 338 (e.g., a cantilever axle). The central axle 338 is coupled to the elongate housing 312 (not shown because that portion of the elongate housing is removed in FIGS. 7 and 8). The central axle 338 extends along axis Q (illustrated in FIG. 4). In the embodiment illustrated in FIGS. 7 and 8, the central axle 338 extends through a portion of the second cam 350, such as through a central portion of the second cam. The second cam 350 is movable about (or around) the central axle 338 (and thus about axis Q, illustrated in FIG. 4), as described in more detail herein.

As described above, the frame 336, which is coupled to the first cam 330, includes the central arm 346. The central arm 346 is movable with respect to the first and second supporting arms 342, 344. As illustrated in FIGS. 7 and 8, the central arm 346 is adapted to rotate about a first end axle 343 (shown in dashed lines in FIG. 8A) associated with the first supporting arm 342 and about a second end axle 345 (shown in dashed lines in FIG. 8A) associated with the second supporting arm 344. As such, the central arm 346 of the frame 336 can rotate about (or with respect to) axis L. Because the central arm 346 is coupled to the first cam 330, which is coupled to the actuator 322, the central arm is moved or rotated about axis L by moving the actuator along axis Q (or about axis L) in the first direction or in the second direction different than the first direction along axis Q.

The steering mechanism 310 includes a protrusion 348. In some embodiments, the protrusion 348 extends from the central arm 346 of the frame 336. In the embodiment illustrated in FIGS. 7 and 8, the protrusion is a swivel pin 348 disposed on and extending from the central arm 346 of the frame 336. Because the swivel pin 348 is disposed on the central arm 346, the swivel pin moves with the central arm 346 when the central arm moves in response to movement of the actuator 322.

The swivel pin 348 extends from the central arm 346 at least partially through a recess 356 (or aperture) defined by the second cam 350. The swivel pin 348 is adapted to move the second cam 350 as the swivel pin is moved in response to movement of the actuator 322. Although the protrusion is illustrated and described as being a swivel pin 348, in other embodiments, the protrusion can have any known configuration or shape suitable for extending through the recess defined by the second cam and/or for moving the second cam.

The second cam 350 is movable between at least a first position (illustrated in FIGS. 7 and 8) and a second position different than the first position. In the embodiment illustrated in FIGS. 7 and 8, the second cam 350 is movable between at least the first position, second position, and a third position different than the first and second positions, as described in more detail below.

The second cam 350 is coupled to each of the third wire 352 and the fourth wire 354. As illustrated in FIGS. 7 and 8, the third and fourth wires 352, 354 are coupled to the second cam 350 at spaced locations. The third wire 352 and the fourth wire 354 are each adapted to move in response to movement of the second cam 350. Additionally, the third and fourth wires 352, 354 are each coupled to the second cam 350 and to the elongate member 302. Thus, movement of the second and third wires 352, 354 moves the elongate member 302, as described in more detail herein.

Referring to FIGS. 7-8 and 12-14, as the actuator 322 is moved in its first direction along axis Q (or about axis L), as indicated by arrow $A_3$, the central arm 346 of the frame 336 moves (or rotates) in a first direction $A_1$ about axis L $A_N$ and about the first and second end axles 343, 345 associated with the first and second supporting arms 342, 344, respectively.

The swivel pin 348 disposed on the central arm 346 moves with the central arm in the first direction. For example, in some embodiments, the central arm 346 rotates downwardly when moved in the first direction. As the swivel pin 348 moves in its first direction, the swivel pin contacts or engages a first surface area 357 of the second cam 350 defining the recess 356. As the swivel pin 348 continues moving in its first direction, the swivel pin pushes against, or otherwise applies force to, the first surface area 357 of the recess 356, and thus causes the second cam 350 to rotate about the central axle 338 and move from its first position towards its second position.

As the second cam 350 moves towards its second position, the second cam moves (or pulls on) the third wire 352. Because the third wire 352 is also coupled to the elongate member 302, the third wire moves the steerable portion 308 of the elongate member in its first direction along the second plane (e.g., to the right).

To return the elongate member 302 to its starting or relaxed position, the actuator 322 is moved in its second direction along axis Q (or about axis L) until the second cam 350 is moved (or returned) to its first position. In some embodiments, the second cam 350 is biased towards its first (or starting) position.

As the actuator 322 is moved in its second direction along axis Q (or about or around axis L), as indicated by arrow $A_4$, the central arm 346 of the frame 336 moves (or rotates) in a second direction different than the first direction about axis L and about the axles 343, 345 associated with the first and second supporting arms 342, 344. For example, in some embodiments, the central arm 346 rotates upwardly when moved in the second direction.

The swivel pin 348 disposed on the central arm 346 moves with the central arm in the second direction. As the swivel pin 348 moves in its second direction, the swivel pin contacts or engages a second surface area 358 of the second cam 350 defining the recess 356. As the swivel pin 348 continues moving in its first direction, the swivel pin pushes against, or otherwise applies force to, the second surface area 358 of the recess 356, and thus causes the second cam 350 to rotate about the central axle 338 and move from at least one of its first position or its second position to or towards its third position.

As the second cam 350 moves towards its third position, the second cam moves (or pulls on) the fourth wire 354. Because the fourth wire 354 is also coupled to the elongate member 302, the fourth wire 354 moves the steerable portion 308 of the elongate member 302 in its second direction along the second plane (e.g., to the left).

The second cam 350 is adapted to introduce force leverage (or a mechanical advantage) to help move the elongate member 302 along the second plane when the steering mechanism 310 is operated. Because the second cam 350 moves by rotating about axis Q, the second cam is adapted to introduce force leverage; for example, to the third wire 352 and/or the fourth wire 354 as the second cam moves between its first, second, and/or third positions.

As the actuator 322 moves in its first direction or its second direction along axis Q (or about axis L), the first cam 330 also correspondingly moves in the same direction. This movement, however, does not necessarily cause the first cam 330 to move between its first, second, or third positions. Thus, movement of the actuator to move the steerable portion 308 of the elongate member 302 along the second plane does not necessarily also move the steerable portion along the first plane. As a result, the first cam 330 and the second cam 350 are independently actuatable (or movable) between their respect first, second, and third positions.

Although the first cam 330 and the second cam 350 are independently actuatable, as previously described, a user can selectively actuate the first and second cams substantially simultaneously. For example, the first and second cams 330, 350 can be actuated substantially simultaneously by moving the actuator 322 along axis L and axis Q at substantially the same time. Movement of the actuator 322 along axis L and axis Q at substantially the same time results in movement of the actuator along a third axis different than axis L and axis Q. For example, the third axis can be at a 45 degree angle to axis : and/or axis Q. As the actuator 322 moves along the third axis, the first and second cams 330, 350 are substantially simultaneously moved, and thus the steerable portion 308 of the elongated member 302 is moved on a third plane different than the first and second planes. For example, the third plane can be at a 45 degree angle to the first and second planes.

Figure 15:
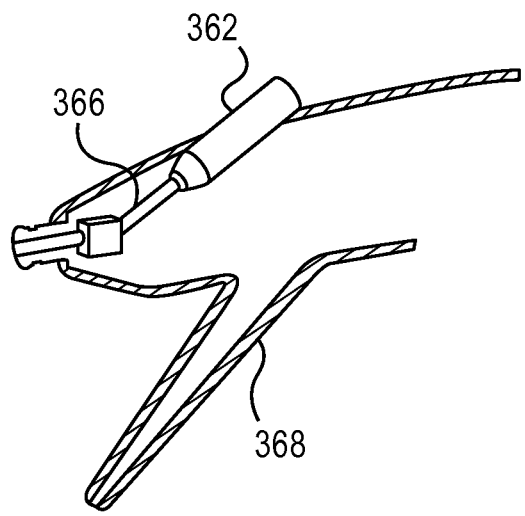
FIG. 15 is a side view of a portion of the medical device of FIG. 3 with a portion of the elongate housing removed.

In some embodiments, as illustrated in FIGS. 5 and 15, the apparatus 300 includes a port 362. The port 362 is adapted to be connected to a working channel 366, or lumen, that extends through at least a portion of the elongate member 302 of the medical device 300 to or towards the distal end portion 306 of the elongate member 302. In some embodiments, the working channel 366 extends to or towards a treatment site in a body of a patient. The port 362 is adapted to receive medical instrumentation. For example, in some embodiments, the port 362 is adapted to receive at least one of a guidewire, laser fiber, stone basket, biopsy device, or other medical instrumentation. The port 362 allows a user to insert the medical instrumentation into the working channel 366, and then through the elongate member 302 to the treatment site. In one procedure, for example, a portion of a guidewire is passed through the port 462, through the working channel 366, and to the treatment site.

FIGS. 16-24 illustrate a steering mechanism 410 according to another embodiment of the invention. The steering mechanism 410 is adapted to control movement (or articulation) of at least a portion of a steerable member of a medical device (not shown in FIGS. 16-24), such as the elongated member 302 described above. In some embodiments, the steering mechanism 410 is configured to move the steerable member along a first plane and along a second plane different than the first plane such that 360 degree articulation of the steerable member is achievable.

The steering mechanism 410 is adapted to be coupled to the steerable member. In some embodiments, the steering mechanism 410 is removably coupled to the steerable member. The steering mechanism 410 includes an elongate housing 412 and an actuation system 470.

The elongate housing 412 includes a proximal end portion 414 and a distal end portion 416. The elongate housing 412 of the steering mechanism 410 is couplable to the steerable member. For example, a distal end portion 416 of the elongate housing 412 (illustrated in FIG. 16) is adapted to be coupled to the steerable member. The distal end portion 416 of the elongate housing 412 is couplable to the steerable member by any known coupling mechanism, including, but not limited to, an interference fit, an adhesive, mating recesses, or the like, or any combination of the foregoing.

The elongate housing 412 is similar in many respects to the elongate housing 312 previously described in reference to FIGS. 3 and 4. For example, the elongate housing 412 is adapted to be held by a user in at least two different orientations. In another example, the elongate housing 412 includes a portion substantially extending along axis L (shown in FIG. 23) and a portion substantially extending along an axis different than axis L (not shown).

The actuation system 470 is coupled to and at least partially disposed within the elongate housing 412. The actuation system 470 is adapted to control movement of a steerable portion of the medical device along at least the first plane and the second plane different than the first plane. The actuation system 470 is also adapted for one-fingered operation by a user.

Referring to FIGS. 16-23, the actuation system 470 includes an actuator 422, a first cam 430, a second cam 450, first and second Bowden cables 474, 476, respectively, a coupling 444, a protrusion 448, and first, second, third, and fourth wires 432, 434, 452, 454, respectively. In other embodiments, the actuation system can include any combination of the foregoing.

The actuator 422 is coupled to the elongate housing 412. In the illustrated embodiment, the actuator 422 is coupled to a portion of the elongate housing 412 between a first grip portion 418 and a second grip portion 420 of the elongate housing. The actuator 422 is movable with respect to the elongate housing 412.

The actuator 422 is adapted for one-fingered use by the user. The actuator 422 is adapted to control movement of a portion of the steerable member of the medical device along at least the first plane and the second plane. As such, the steerable portion 408 of the steerable member is movable in substantially any direction 360 degrees around the central axis C.

In the embodiment illustrated in FIGS. 16-23, the actuator 422 includes a finger rest portion 428 and a stem 426. The finger rest portion 428 is illustrated as being substantially U-shaped, however, in other embodiments, the finger rest portion can be any known shape suitable for use as part of a medical device. The U-shape (or contour) of the finger rest portion 428 allows a user's finger to rest easily and comfortably on the actuator 422. The contour of the finger rest portion 428 is adapted to help prevent the user's finger from slipping off of either side of the finger rest portion of the actuator. The stem 426 couples the finger rest portion 428 of the actuator 422 to the actuation system 470 and the elongate housing 412.

Figure 17:
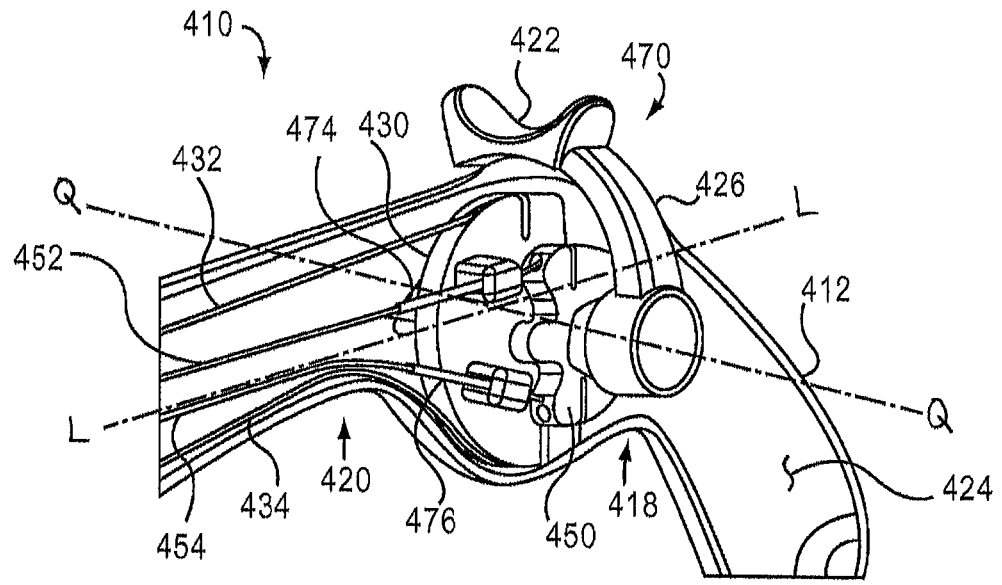
FIGS. 17 and 18 are perspective views of a portion of the steering mechanism of FIG. 16 with a portion of the elongate housing removed.
Figure 23:
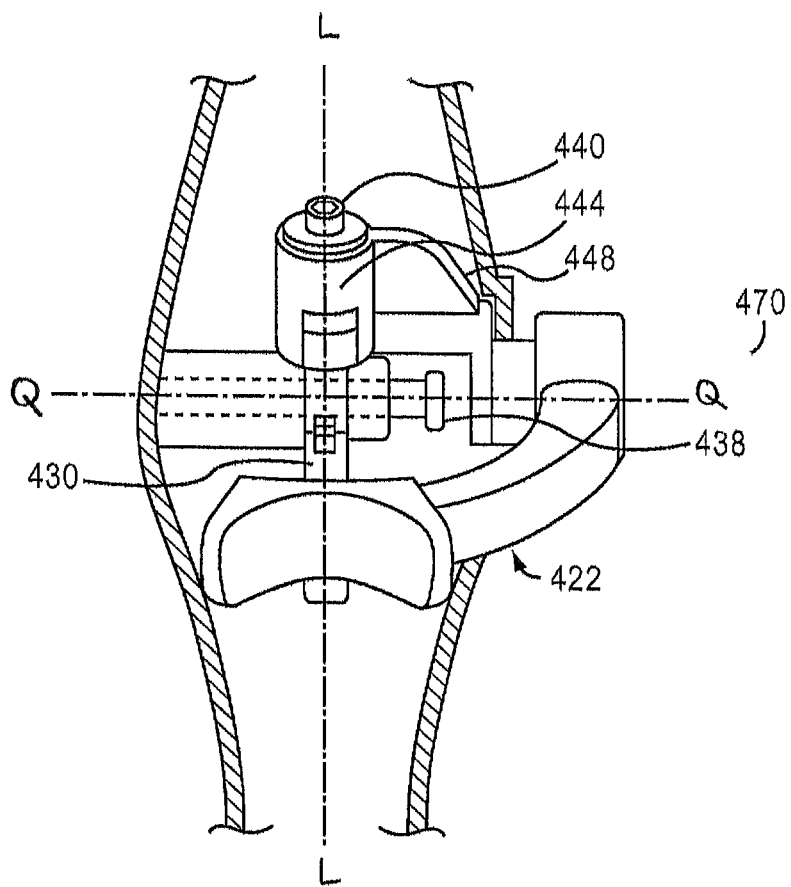
FIG. 23 is a top view of a portion of the steering mechanism of FIG. 16 with the second cam and a portion of the housing removed.

The actuator 422 is adapted to move along axis L and along axis Q different than axis L, as illustrated in FIGS. 17 and 23. As described herein, the actuator 422 is adapted to move each of the first cam 430 and the second cam 450. The first cam 430 is adapted to move the steerable member of the medical device along the first plane when the first cam 430 is moved by the actuator 422. The second cam 450 is adapted to move the steerable member of the medical device along the second plane when the second cam 450 is moved by the actuator 422.

As illustrated in FIG. 17, the first cam 430 is at least partially disposed in a cavity 424 defined by the elongate housing 412. The first cam 430 is coupled to the elongate housing 412. As illustrated in FIG. 23, in some embodiments, the first cam 430 is coupled to the elongate housing 412 by an axle 438 (a portion of which is shown in dashed lines). In some embodiments, the axle 438 is a cantilever axle. The axle 438 extends from the elongate housing 412 along axis Q into the cavity 424 of the elongate housing. The axle 438 at least partially extends through an opening (not shown) defined by the first cam 430. The first cam 430 is movable about (or around) axis Q along which the axle 438 extends, as described in more detail below. The first cam 430 is movable between at least a first position (illustrated in FIGS. 17 and 18) and a second position (illustrated in FIG. 19) different than the first position. In the embodiment illustrated in FIGS. 17 and 18, the first cam 430 is movable between at least the first position, the second position different than the first position, and a third position (illustrated in FIG. 20) different than the first and second positions, as described in more detail below.

The first cam 430 is coupled to a second axle 440 of the steering mechanism 410. The axle 440 is disposed within the cavity 424 defined by the elongate housing 412. In the embodiment illustrated in FIG. 23, the axle 440 extends along axis L. The actuator 422 is coupled to the axle 440 by a coupling 444. As illustrated in FIG. 23, in some embodiments, the coupling 444 is disposed over at least a portion of the axle 440.

Figure 18:
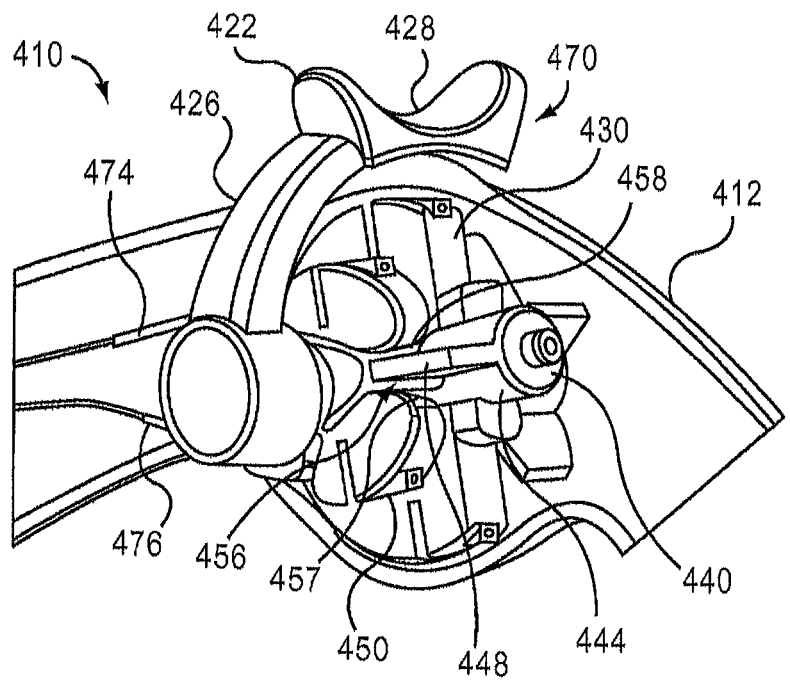
Figure 19:
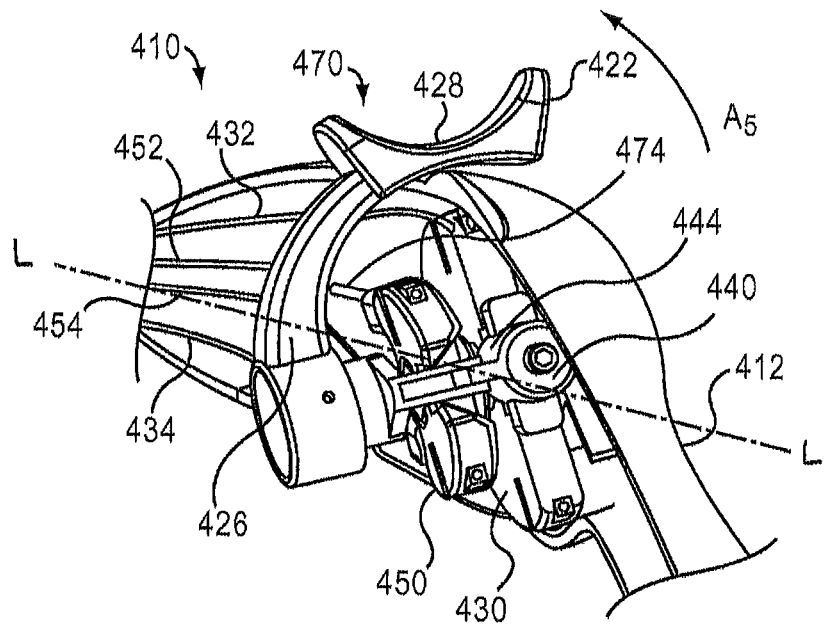
FIGS. 19-22 are perspective views of a portion of the steering mechanism of FIG. 16 with a portion of the elongate housing removed and in a first configuration, a second configuration, a third configuration, and a fourth configuration, respectively.
Figure 20:
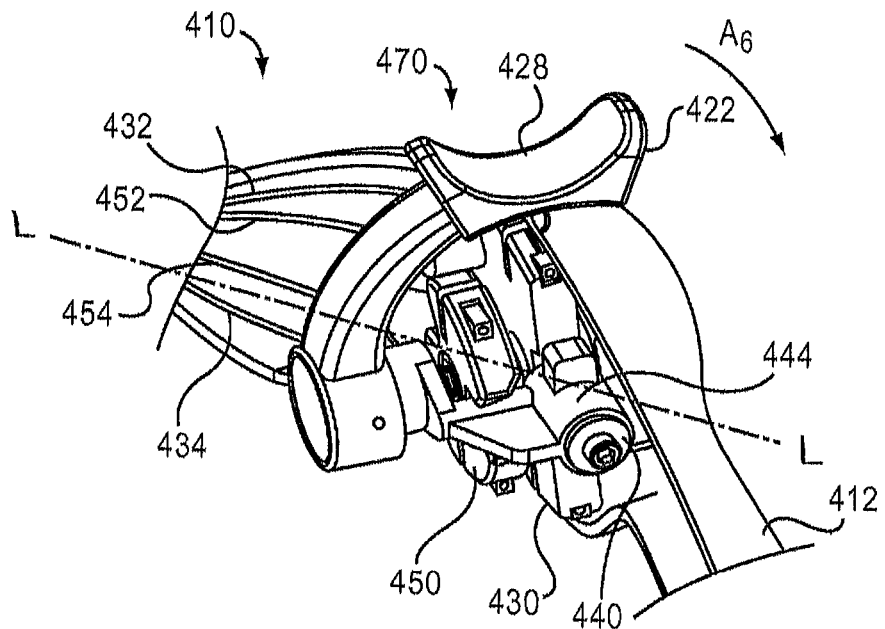

As the actuator 422 is moved in its first direction (e.g., as indicated by arrow $A_5$ in FIG. 19) along axis L (or about axis Q), the coupling 444 is moved in the first direction, thus the axle 440 is moved in the first direction and the first cam 430, which is coupled to the axle 440, is moved (or rotated) about axis Q from its first position (illustrated in FIG. 18) to its second position (illustrated in FIG. 19). In other words, movement of the actuator 422 in its first direction along axis L moves the first cam 430 from its first position to its second position.

The first wire 432 and the second wire 434 are each coupled to the first cam 430. In the embodiment illustrated in FIGS. 17 and 18, the first wire 432 and the second wire 434 are coupled to the first cam 430 at spaced locations. Each of the first wire 432 and the second wire 434 is adapted to move in response to movement of the first cam 430. The first and second wires 432, 434 are each also coupled to the steerable member (not illustrated).

As the first cam 430 moves about axis Q from its first position to or towards its second position, the first cam moves (or pulls on) the first wire 432, and thus the first wire 432 moves the steerable portion of the steerable member in its first direction along the first plane (e.g., "up").

To return the steerable member to its starting or relaxed position, the actuator 422 is moved in its second direction (e.g., as indicated by arrow $A_6$ in FIG. 20) until the first cam 430 is moved (or returned) to its first position. In some embodiments, at least one of the actuator 422 and the first cam 430 is biased towards a first (or starting) position.

As the first cam 430 moves from its first position towards its third position, the first cam moves (or pulls on) the second wire 434. The second wire 432 moves the steerable portion of the steerable member in its second direction along the first plane (e.g., "down").

As illustrated in FIGS. 17 and 18, the second cam 450 is disposed in the cavity 424 of the elongate housing 412. The second cam 450 is at least partially disposed over the axle 438. Said another way, the axle 438 at least partially extends through a portion of or opening defined by the second cam 450, such as a central portion of the second cam. The second cam 450 is adapted to rotate about axis Q along which the axle 438 extends. For example, as the first cam 430 is moved in the first direction from its first position and its second position and/or in the second direction from its second position to its first position and/or its third position, the second cam 450 correspondingly moves about axis Q in the first direction and/or the second direction. In this manner, and as described in more detail herein, the relative position of the Bowden cables 474, 476, which are coupled to the first cam 430, remains substantially the same with respect to the third and fourth wires 452, 454, which are coupled to the second cam 450, when the first cam is moved between its first position, second position, and/or third position and the second cam is correspondingly moved in the first direction and/or the second direction. In this manner, articulation of the steerable member of the medical device along the second plane is substantially unaffected by rotation of the second cam 450 about axis Q, that corresponds with rotation of the first cam 430 about axis Q.

The second cam 450 is movable between at least a first position (illustrated in FIGS. 17 and 18) and a second position (illustrated in FIG. 21) different than the first position. In the embodiment illustrated in FIGS. 16-23, the second cam 450 is movable between the first position, the second position, and a third position (illustrated in FIG. 22) different than the first and second positions, as described herein.

The second cam 450 and the first cam 430 can be independently movable. For example, the second cam 450 is adapted to move the steerable member along the second plane when the second cam is moved (or rotated) about axis Q independently of movement (or rotation) of the first cam 430 about axis Q, as described herein.

As described above, the actuation system 470 includes the coupling 444. The coupling 444 is movable with respect to the axle 440. For example, the coupling 444 can be adapted to rotate with respect to (or about) the axle 440 (and about axis L along which the axle 440 extends). In the embodiment illustrated in FIGS. 17-23, the coupling 444 is a T-shaped coupling.

At least a portion of the coupling 444 is adapted to engage the second cam 450. In the embodiment illustrated in FIG. 18, the protrusion 448 is a lever portion that extends from the coupling 444 at least partially through a recess 456 (or aperture) defined by the second cam 450. The lever portion 448 is adapted to move in response to movement of the actuator 422. The lever portion 448 is adapted to move the second cam 450 as the lever portion moves in response to movement of the actuator 422, as described in more detail herein.

The third wire 452 and the fourth wire 454 are each coupled to the second cam 450. In the embodiment illustrated in FIGS. 17 and 18, the third and fourth wires 452, 454 are coupled to the second cam 450 at spaced locations. The third and fourth wires 452, 454 are each also coupled to the steerable member. The third and fourth wires 452, 454 are adapted to be moved by the second cam 450 and to move the steerable member along the second plane in response to movement of the second cam.

At least a portion of each of the third and fourth wires 452, 454 are disposed within a lumen defined by the first and second Bowden cables 474, 476, respectively. The first and second Bowden cables 474, 476 are adapted to help transfer the point of relative motion from distal end portions of the third and fourth wires 452, 454 to a more proximal portion of the wires 452, 454. For example, the third wire 452 can move relative to the first Bowden cable 474 to move (or articulate) the steerable member in the first direction along the second plane.

The first and second Bowden cables 474, 476 can be constructed of any suitable material. For example, the Bowden cables 474, 476 can be of a composite construction, such as a spiral steel wire coated with plastic. The Bowden cables 474, 476 can include an outer sheath, such as a plastic outer sheath. The first Bowden cable 474 terminates on a portion of the first cam 430, as illustrated in FIG. 17. The second Bowden cable 476 terminates on a portion of the first cam 430, as also illustrated in FIG. 17.

Figure 21:
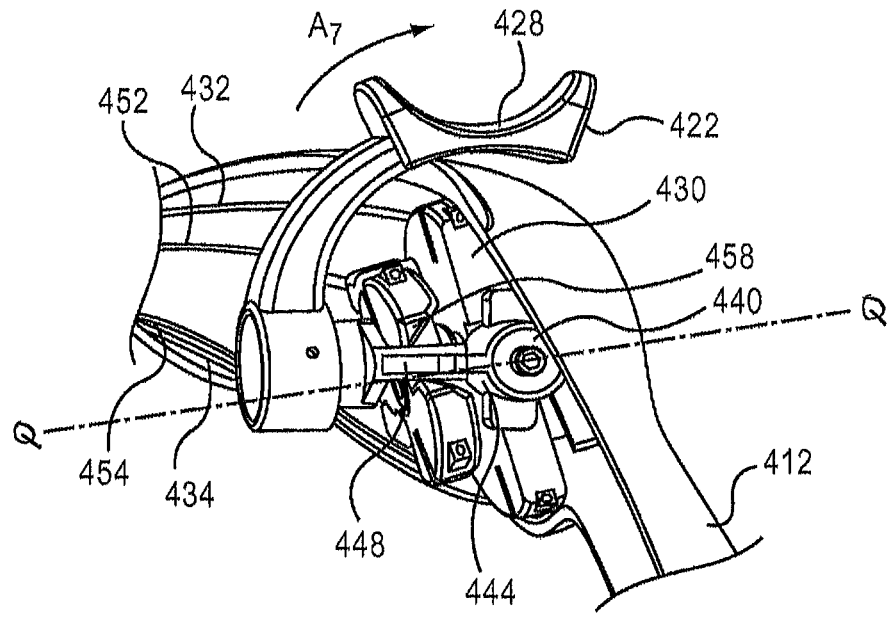

Referring to FIG. 21, as the actuator 422 moves in its first direction (e.g., as indicated by arrow $A_7$) along axis Q (or about axis L), the coupling 444 rotates in a first direction about the axle 440 from a first position to a second position different than the first position. As the coupling 444 rotates in the first direction to or towards its second position, the lever portion 448 moves in the first direction from a first position to or towards a second position different than its first position. As the lever portion 448 moves to or towards its second position, the lever portion engages or contacts a first surface area 457 of the second cam 450 at least partially defining a recess 456.

As the lever portion 448 continues moving in its first direction, the lever portion pushes against, or otherwise applies force to, the first surface area 457 of the second cam 450 defining the recess 456, and thus causes the second cam 450 to move from its first position towards its second position.

As the second cam 450 moves towards its second position, the second cam moves (or pulls on) the third wire 452. Because the first cam 430 does not move about the axle 438 with the second cam 450, the first Bowden cable 474 remains relatively stationary and the third wire 452 moves with respect to the first Bowden cable. The linear movement of the third wire 452 relative to the first Bowden cable 474 transmits a moving (or pulling) force to the third wire. Thus, the third wire 452 moves the steerable member in its first direction along the second plane (e.g., to the right).

To return the steerable member to the linear or relaxed position, the actuator 422 is moved in its second direction (e.g., as indicated by arrow $A_8$ in FIG. 22) along axis Q (or about axis L) until the second cam 450 is moved (or returned) to its first position. In some embodiments, the second cam 450 is biased towards its first (or starting) position.

Figure 22:
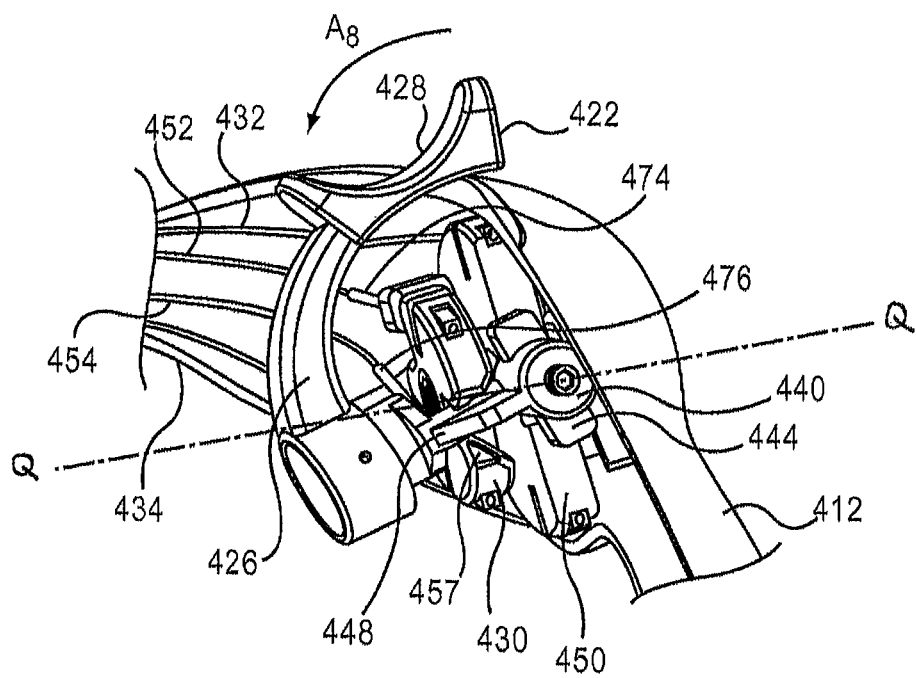

Referring to FIG. 22, the second cam 450 is moved to or towards its third position by moving the actuator 422 in its second direction along axis Q. As the actuator moves in its second direction along axis Q, the coupling 444 rotates in a second direction different than its first direction about the axle 440 from one of its first or second positions to a third position different than its first or second positions. As the coupling 444 rotates in the second direction to or towards its third position, the lever portion 448 is moved in the second direction from its first or second position to a third position different than its first or second positions. As the lever portion 448 moves to or towards its third position, the lever portion engages or contacts a second surface area 458 of the second cam 450 at least partially defining the recess 456.

As the lever portion 448 continues moving in its second direction, the lever portion pushes against, or otherwise applies force to, the second surface area 458 of the second cam 450, and thus causes the second cam to move from at least one of its first or second positions to or towards its third position.

As the second cam 450 moves towards its third position, the second cam moves (or pulls on) the fourth wire 454. Because the first cam 430 does not move about the axle 438 with the second cam 450, the second Bowden cable 476 remains relatively stationary and the fourth wire 454 moves with respect to the second Bowden cable. The linear movement of the fourth wire 454 relative to the second Bowden cable 476 transmits a moving (or pulling) force to the fourth wire. Thus, the fourth wire 454 moves the steerable portion 308 of the steerable member in its second direction along the second plane (e.g., to the left).

The steering mechanism 410 has been illustrated and described as including first and second Bowden cables 474, 476 associated with movement of the steerable member along the second plane, however, in other embodiments, the Bowden cables can be associated with movement of the steerable member along the first plane. In such an embodiment, the Bowden cables will terminate at a proximal end of each cable on an inner portion of the elongate housing. In other embodiments, the steering mechanism can include any number of Bowden cables, such as a Bowden cable associated with each wire included in the steering mechanism, or none.

Although the first and second Bowden cables 474, 476 terminate on the first cam 430, and thus move with the first cam when the first cam moves between its first, second, and third positions, there is no relative movement between the third or fourth wire 452, 454 and their respective Bowden cables because the second cam 450 also moves with the first cam as the first cam moves in its first or second directions along axis L (or about axis Q). As such, movement of the first actuator to move the steerable member along the first plane does not cause inadvertent movement of the steerable member along the second plane.

Although the first cams 330, 430 have been illustrated as being larger in size than the second cams 350, 450, respectively, in other embodiments, the first cam and second cam can each be a different size. For example, in one embodiment, the first and second cams are the same size. In another example, the second cam is larger in size than the first cam.

Although the steering mechanism 310, 410 has been illustrated and described as including first, second, third, and fourth wires 332, 334, 352, 354 and 432, 434, 452, 454, respectively, in other embodiments, the steering mechanism includes a different number of wires. For example, in one embodiment, the steering mechanism includes a first wire and a second wire. In such an embodiment, the first wire is adapted to move the steerable member along the first plane, and the second wire is adapted to move the steerable member along the second plane. For example, in one such embodiment, the ends of the first wire are coupled to a steerable member of a medical device and a portion of the first wire between its ends is coupled to a first cam. In some embodiments, a portion of the first wire between its ends is wrapped around a portion of the first cam. As the first cam is moved between its first, second and third positions, the first cam moves one of the ends of the first wire coupled to the steerable member resulting in articulation of the steerable member. The ends of the second wire are coupled to the steerable member and a portion of the second wire between its ends is coupled to a second cam. In some embodiments, a portion of the second wire between its ends is wrapped around a portion of the second cam. As the second cam is moved between its first, second and third positions, the second cam moves one of the ends of the second wire coupled to the steerable member resulting in articulation of the steerable member.

Although the steering mechanism 310, 410 has been illustrated and described as moving the steerable (or elongate) member along a vertical plane and a horizontal plane, in other embodiments, the steering mechanism moves the steerable member along at least two planes different than the vertical and horizontal planes.

Figure 16:
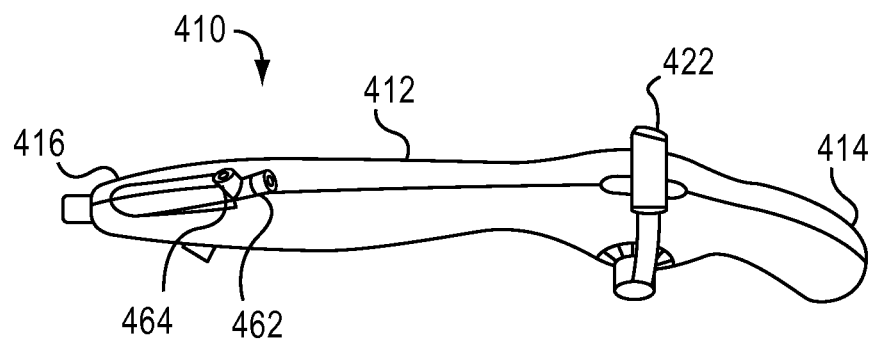
FIG. 16 is a top view of a steering mechanism according to an embodiment of the invention.
Figure 24:
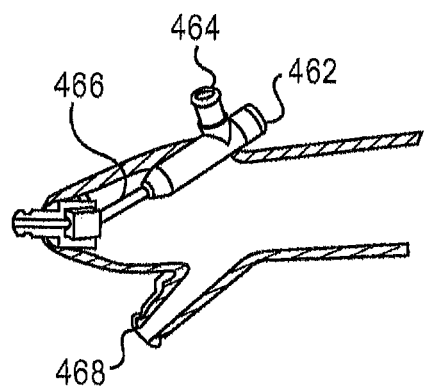
FIG. 24 is a side view of a portion of the steering mechanism of FIG. 16 with a portion of the elongate housing removed.

In some embodiments, as illustrated in FIGS. 16 and 24, the steering mechanism 410 includes a first port 462 and a second port 464. The first port 462 is substantially similar to the first port 362 described above with reference to FIGS. 5 and 15. The second port 464 is adapted to transport an irrigation fluid, such as saline, or gas, such as an air jet, from a source external to the medical device 400 into the first port 462. The second port 464 is fluidically connected to the first port 462, which can be fluidically connected to the working channel 466 extending at least partially through the elongate member. The irrigation fluid can be passed through the second port 464 to wash the medical instrumentation passed through the first port 462. In one procedure, for example, an irrigation fluid is passed through the second port 464 to wash off debris, such as from broken stones being removed from the treatment site by a stone basket that has been passed through the first port 462.

In the illustrated embodiment, the second port 464 extends radially from the first port 462. In some embodiments, the ports 462, 464 are configured with a Y-shaped junction, as illustrated in FIG. 24. One or both of ports 462, 464 can be monolithically constructed with the elongate housing 412. In other embodiments, one or both of ports 462, 464 can be separately constructed and then disposed on or coupled to the elongate housing 412. Although ports 462, 464 are illustrated as being coupled to the distal end portion 416 of the elongate housing 412, in other embodiments, the ports can be coupled to a different portion of the medical device 400.

Referring again to FIGS. 15 and 24, in some embodiments, the medical device includes or is adapted to receive an electrical component (not shown). For example, the steering mechanism 310, 410 includes an electrical port 368, 468. The electrical port 368, 468 is adapted for channeling or receiving at least a portion of the electrical component. For example, in some embodiments, the electrical port is adapted to receive at least a portion of a signal transmission line. In one procedure, the signal transmission line can extend from a point exterior to the medical device, through the electrical port, and through the elongate member to or towards the distal end portion of the elongate member. The signal transmission line, for example, can be adapted to transmit an image received by an optical element at the distal end portion of the transmission line to an imaging system exterior to the medical device. In another example, the electrical port is adapted to receive at least a portion of an electrical component including a fiber optic light and associated electrical cable. In some embodiments, the electrical port is monolithically constructed with the elongate housing. In other embodiments, the electrical port is separately constructed and then coupled to the elongate housing. Although the electrical port is illustrated as being coupled to the distal end portion of the elongate housing, in other embodiments, the port can be coupled to a different portion of the medical device.

Although the steering mechanism 310 is illustrated and described as including first port 362 and electrical port 368, and the steering mechanism 410 is illustrated and described as including first port 462, second port 464, and electrical port 368, in other embodiments, a steering mechanism can include any combination of the first, second, and electrical ports, only one of the first, second, or electrical ports, or none.

In a procedure utilizing a steering mechanism according to the present invention, a user operatively holds the elongate housing of the steering mechanism in a hand of the user. To hold the elongate housing, the user can grasp one of the first grip portion or the second grip portion with the user's hand. The user places a finger of the hand holding the elongate housing onto the actuator. For example, the user can place a pad of the finger on the finger rest portion of the actuator.

The user moves the actuator with the finger on the actuator in a first direction along axis L defined by a portion of the elongate housing of the steering mechanism. Moving the actuator in the first direction along axis L includes moving a first cam in a first direction and moving a steerable portion of a medical device in a first direction along a first plane. For example, to move the steerable member or portion of the medical device in a vertical direction, the user moves the actuator along axis L.

The user moves the actuator in a first direction along an axis different than axis L defined by a portion of the elongate housing of the steering mechanism. For example, the user can move the actuator along an axis transverse to axis L. Moving the actuator in the first direction along the axis different than axis L includes moving a second cam in a first direction and moving the steerable portion of the medical device in a first direction along a second plane different than the first plane. For example, to move the steerable member or portion in a horizontal direction, the user moves the actuator to the left or to the right (along axis Q) from the perspective of the user.

The user can move the steerable member in a direction other than a vertical or horizontal direction by moving the actuator along axis L and axis Q substantially the same time. For example, the user can substantially simultaneously move the actuator along both of the longitudinal and transverse axes to move the steerable member or portion at a 45 degree angle. The user can also achieve articulation of the steerable member or portion at the 45 degree (or other) angle by sequentially moving the actuator along axis L and axis Q. The steering mechanism is configured such that the user can control articulation of the steerable member or portion in substantially any angle or direction that is 360 degrees about axis L. The 360 degree articulation allows the user to approximate the distal end portion of the steerable member to a desired location within a body of a patient.

Although the features of the steerable medical device, and the steering mechanism particularly, have been illustrated and described in certain combinations, in other embodiments, individual features can be combined or not included in a particular embodiment. For example, in another embodiment, the steering mechanism 310 can include Bowden cables like those illustrated and described with respect to the steering mechanism 410.

In another example, the steering mechanism 310 can include a protrusion that is a lever portion similar to the lever portion 448 illustrated and described with respect to the steering mechanism 410; for example, instead of the swivel pin 348. In a further example, the protrusion can be disposed on a different portion of the steering mechanism; for example, on the elongate housing.

Additionally, although the second axis has been illustrated as being substantially normal to axis L, in other embodiments, the other can be at a different angle to axis L.

While various embodiments of the invention have been described above, it should be understood that they have been presented by way of example only and are not limiting on the invention. Thus, the breadth and scope of the invention should not be limited by any of the above-described embodiments, but should be defined only in accordance with the claims and their equivalents.

What is claimed is:

1. A steering mechanism for use as part of a medical device, comprising:
   an elongate housing adapted to be coupled to a steerable member of a medical device; and
   an actuation system coupled to the elongate housing, the actuation system adapted to control movement of the steerable member of the medical device within a body of a patient, the actuation system including an actuator, a first cam, and a second cam, wherein:
   the actuator is adapted to move the first cam from a first position to a second position different than the first position when the actuator is moved in a first direction about a first axis,
   the first cam is adapted to move the steerable member of the medical device in a first direction along a first plane when the first cam is moved from the first position to the second position,
   the actuator is adapted to move the second cam from a first position to a second position different than the first position when the actuator is moved in a first direction about a second axis different than the first axis,
   the second cam is adapted to move the steerable member of the medical device in a first direction along a second plane when the second cam is moved from the first position to the second position, and
   the first cam is adapted to move about the first axis and the second axis, and the first cam and the second cam are adapted to rotate about the first axis,
   wherein the elongate housing includes a first grip portion and a second grip portion different than the first grip portion, and the actuator is coupled to the elongate housing between the first grip portion and the second grip portion.

2. The steering mechanism of claim 1, further comprising a protrusion coupled to the first cam, the protrusion adapted to move in a first direction when the actuator is moved in its first direction about the second axis, the protrusion adapted to engage a portion of the second cam at least partially through a recess defined by the second cam as the protrusion is moved in its first direction.

3. The steering mechanism of claim 2, wherein the protrusion is adapted to move the second cam from its first position to its second position as the protrusion is moved in the first direction.

4. The steering mechanism of claim 1, wherein the actuation system is adapted for one-fingered operation by a user.

5. The steering mechanism of claim 1, wherein the elongate housing is adapted to be in a first orientation when operatively held by the first grip portion, and the elongate housing adapted to be in a second orientation different than the first orientation when operatively held by the second grip portion.

6. The steering mechanism of claim 1, wherein the elongate housing includes a proximal end portion and a distal end portion that each extend along an axis, wherein the axis of the proximal end portion is offset from the axis of the distal end portion.

7. The steering mechanism of claim 1, wherein the actuator is adapted to move the first cam from its second position to at least one of the first position or a third position different than the first position when the actuator is moved in a second direction different than the first direction about the first axis, the first cam adapted to move the steerable member in a second direction different than the first direction along the first plane when the first cam is moved from the second position to the at least one of the first position or the third position.

8. The steering mechanism of claim 1, wherein the actuator is adapted to move the second cam from the second position to at least one of the first position and a third position different than the second position when the actuator is moved in a second direction different than the first direction about the second axis, the second cam adapted to move the steerable member in a second direction different than the first direction along the second plane when the second cam is moved from the second position to the at least one of the first position or the third position.

9. The steering mechanism of claim 1, wherein the first cam is adapted to be moved from its first position to its second position independently of movement of the second cam from its first position to its second position.

10. The steering mechanism of claim 1, wherein the second cam is adapted to be moved from its first position to its second position independently of movement of the first cam from its first position to its second position.

11. The steering mechanism of claim 1, further comprising:
   a Bowden cable disposed over a portion of a wire coupled to the actuator, the Bowden cable adapted to move relative to the wire when the wire is moved in response to movement of the actuator.

12. The steering mechanism of claim 1, wherein the actuator is movable in the first direction about the first axis and in the first direction about the second axis substantially simultaneously.

13. A steering mechanism for use with or as part of a medical device, comprising:

a housing adapted to be coupled to a medical device including a steerable portion;

an actuator coupled to the housing, the actuator movable with respect to the housing in a first direction about a first axis, the actuator movable with respect to the housing in a first direction about a second axis different than the first axis;

a first cam movable in response to movement of the actuator in the first direction about the first axis and in the first direction about the second axis, the first cam adapted to move the steerable portion of the medical device along a first plane;

a second cam movable in response to movement of the actuator in the first direction about the second axis, the second cam adapted to move the steerable portion of the medical device along a second plane different than the first plane; and a protrusion coupled to the first cam, the protrusion adapted to move in a first direction when the actuator is moved in its first direction about the second axis, the protrusion adapted to engage a portion of the second cam at least partially through a recess defined by the second cam as the protrusion is moved in its first direction to cause rotation of the second cam about the first axis.

14. The steering mechanism of claim 13, wherein the actuator is adapted for one-fingered operation by a user.

15. The steering mechanism of claim 13, wherein the protrusion is adapted to move the second cam from a first position to a second position different than the first position, the second cam adapted to move the steerable portion of the medical device in a first direction along the second plane as the second cam moves from its first position to its second position.

16. The steering mechanism of claim 13, further comprising:

a wire coupled to the actuator, the wire adapted to move the steerable portion of the medical device; and a Bowden cable disposed over at least a portion of the wire, the wire movable with respect to the Bowden cable.

17. A steering mechanism for use as part of a medical device, comprising:

an elongate stationary housing adapted to be coupled to a steerable member of a medical device; and an actuation system coupled to the elongate stationary housing, the actuation system adapted to control movement of the steerable member of the medical device within a body of a patient, the actuation system including an actuator, a first cam, and a second cam, wherein:

the actuator is adapted to move the first cam about a first axis from a first position to a second position, the first cam is adapted to move the steerable member of the medical device along a first plane when the first cam is moved from the first position to the second position, the actuator is adapted to move the first cam about a second axis substantially normal to the first axis from a third position to a fourth position, the second cam is adapted to move the steerable member of the medical device along a second plane when the first cam is moved from the third position to the fourth position, and the first cam and the second cam are adapted to rotate about the first axis.

* * * * *